United States Patent [19]

Shubkin et al.

[11] Patent Number: 5,171,918
[45] Date of Patent: Dec. 15, 1992

[54] APPARATUS AND OIL COMPOSITIONS CONTAINING OLEFIN DIMER PRODUCTS

[75] Inventors: Ronald L. Shubkin; Kevin J. Theriot, both of Baton Rouge, La.

[73] Assignee: Ethyl Corporation, Richmond, Va.

[21] Appl. No.: 705,960

[22] Filed: May 28, 1991

Related U.S. Application Data

[63] Continuation-in-part of Ser. No. 684,291, Apr. 12, 1991, abandoned, which is a continuation-in-part of Ser. No. 554,727, Jul. 19, 1990, Pat. No. 5,068,487.

[51] Int. Cl.⁵ .............................................. C07C 2/06
[52] U.S. Cl. ...................................... 585/510; 585/10; 585/12; 585/255; 252/49.6; 252/73; 252/570
[58] Field of Search ............... 585/10, 510, 525, 255, 585/12; 252/49.6, 570, 73

[56] References Cited

U.S. PATENT DOCUMENTS

| 3,742,082 | 6/1973 | Brennan | 585/510 |
| 3,957,664 | 5/1976 | Hellman et al. | 252/49.6 |
| 4,045,507 | 8/1977 | Cupples et al. | 260/683.15 B |
| 4,205,195 | 5/1980 | Desbois | 585/520 |
| 4,211,665 | 7/1980 | Pellegrini, Jr. | 252/63 |
| 4,238,343 | 12/1980 | Pellegrini, Jr. | 585/24 |
| 4,239,638 | 12/1980 | Beretta et al. | 252/73 |
| 4,584,113 | 4/1986 | Walsh | 252/45 |

Primary Examiner—Anthony McFarlane
Attorney, Agent, or Firm—David M. Bunnell

[57] ABSTRACT

Heat transfer, lubricating, functional and/or insulating fluid compositions for use in apparatus such as electrical transformers contain up to 25 weight percent of one or more oil additives and a 1-octene and/or 1-decene dimer and/or a 1-octene and 1-decene co-dimer oil having improved low temperature properties which oil contains less than about 2.5 weight percent of, respectively, the 7-methylpentadecene, 9-methylnonadecene and, 7- and 9-methylheptadecene isomers. The dimers can be hydrogenated to provide the saturated counterparts of the isomers.

8 Claims, No Drawings

APPARATUS AND OIL COMPOSITIONS CONTAINING OLEFIN DIMER PRODUCTS

RELATED APPLICATION

This application is a Continuation-in-Part of application Ser. No. 684,291, filed Apr. 12, 1991, now abandoned, entitled Olefin Dimer Products which is a continuation-in-part of application Ser. No. 554,727, filed July 19, 1990, now U.S. Pat. No. 5,068,487 both of which applications are incorporated herein by reference.

BACKGROUND

This invention relates generally to alpha-olefin oligomers which are useful as synthetic lubricants and functional fluids and more particularly to apparatus and fluids which contain alpha-olefin dimer products having improved low temperature properties which can be prepared by a $BF_3$-promoter catalyst system using alcohol alkoxylates as promoters.

Alpha-olefin oligomers and their use as synthetic lubricants ("synlubes") are well-known. The oligomers are usually hydrogenated in order to improve their stability. Early reports of such synlubes are in Seger et. al. U.S. Pat. No. 2,500,161 and Garwood U.S. Pat. No. 2,500,163. The particular applications for which such oligomer oils are used depends upon their viscosity, with viscosities of about 2–10 cSt at 100° C. being preferred for general lubricating oil applications. Low viscosity, (e.g. 1–3 cSt at 100° C.) alpha-olefin dimer oils are especially useful in heat transfer, insulating, hydraulic and low temperature lubricant applications.

Co-pending Application Serial No. 554,727 describes a process for preferentially making dimer oils of linear alpha-olefins such as 1-octene and 1-decene by using a catalyst comprising boron trifluoride and an alcohol alkoxylate promoter such as 2-methoxyethanol. This process produces dimer products which have improved low temperature properties compared to dimers prepared using other alcohol promoters such as propanol or butanol. These dimer products of 1-decene or 1-octene remain clear, without precipitation of components at −54° C. The products have a unique isomer content in that they contain undetectable amounts (less than about 0.5% by weight) of, respectively, the nearly straight chain isomers 9-methylnonadecenes and 7-methylpentadecenes or, after hydrogenation of the dimer products, the saturated counterparts of these compounds. In contrast, commercially available hydrogenated dimers prepared, for example, by oligomerizing 1-decene using a $BF_3$-butanol, or $BF_3$-propanol catalyst have a significantly different isomer content than those produced using the alcohol alkoxylate promoters and contain much greater amounts (3 to 5 weight percent) of relatively linear isomers, e.g. 9-methylnonadecane, and become cloudy and exhibit significant viscosity changes at −54° C.

BRIEF SUMMARY

In accordance with this invention there is provided an apparatus containing a heat transfer, lubricating, functional and/or insulating fluid which comprises a dimer of 1-octene which is a mixture of $C_{16}H_{32}$ isomers containing less than about 2.5 weight percent of 7-methylpentadecene isomers and/or a dimer of 1-decene which is a mixture of $C_{20}H_{40}$ isomers containing less than about 2.5 weight percent of 9-methylnonadecane isomers and/or a co-dimer of 1-octene and 1-decene which is a mixture of $C_{18}H_{36}$ isomers containing less than about 2.5 weight percent of the 7-methylheptadecene and/or 9-methylheptadecene isomers.

Also provided is a heat transfer, lubricating, functional and/or insulating fluid composition which comprises (i) a 1-octene and/or a 1-decene dimer and/or a 1-octene and 1-decene co-dimer oil comprising a mixture of isomers which in the case of the 1-octene dimer are $C_{16}H_{32}$ isomers containing less than about 2.5 weight percent of the 7-methylpentadecene isomers, in the case of the 1-decene dimer are $C_{20}H_{40}$ isomers containing less than about 2.5 weight percent of the 9-methylnonadecene isomers, and in case of the co-dimer are $C_{18}H_{36}$ isomers containing less than about 2.5 weight percent of the 7-methylheptadecene and/or 9-methylheptadecene isomers, and (ii) from about 0.1 to 25 weight percent of fluid composition of one or more oil additives. The dimers can be hydrogenated to provide the saturated counterparts of the isomers, i.e. $C_{16}H_{34}$ for the 1-octene dimer, $C_{18}H_{38}$ for the co-dimer and $C_{20}H_{42}$ for the 1-decene dimer.

DETAILED DESCRIPTION

The dimer products useful in this invention are preparable by the process described in co-pending application Ser. No. 554,727. According to the process, the 1-octene or 1-decene linear alpha-olefin monomer or a mixture of such monomers in any proportions is contacted with a catalytic amount of boron trifluoride which should be at least about 0.002 moles per mole of olefin. When a mixture of 1-octene and 1-decene is dimerized some 1-octene and 1-decene dimers are produced besides the co-dimer. Such mixtures can be employed in the invention without separating out the co-dimer. Preferably the reaction mixture is saturated with $BF_3$. The boron trifluoride is used in combination with a promoter which is an alcohol alkoxylate. This promoter surprisingly favors the production of lower oligomers and particularly products containing predominantly dimer and trimer with a dimer to trimer ratio of greater than about one. Under ordinary reaction conditions the dimer does not further react, and particularly does not dimerize, to any significant extent so that the reaction is easily controllable to produce a large proportion (at least about 40 and preferably 50 to 85 weight percent or more dimer based on the total weight of oligomers in the product) of dimer. The dimer content asymptotically approaches a maximum rather than sharply peaking at a transient maximum, which is common in prior processes. The dimer products are a complex mixture of 25 or more isomers (a $C_{20}H_{42}$ paraffin can theoretically have 366,319 possible isomers). There is no absolute method for predicting the isomers most likely to be found in the hydrogenated dimer products of 1-decene products. Accordingly, analysis of all of the isomers by gas chromatography is not practical, especially since peaks can be mixtures of closely related isomers (see Onopchenko, et. al., "$BF_3$-Catalyzed Oligomerization of Alkenes: Structures, Mechanisms, and Properties", Ind. Eng. Chem. Prod. Res. Dev. 1983, 22, 182–191). However, it is possible to identify the more linear isomers such as those having no branches or a single branch with one carbon atom. The dimer products prepared using the alcohol alkoxylate promoters have improved low temperature properties because of their unique isomer content in that they contain less than about 2.5 weight percent and, especially, less than about 0.5 weight percent of relatively linear isomers.

Alcohol alkoxylates useful in the invention can be represented, for example, by the formula:

$$RO(CHR'-CHR''-(CHR''')_m-O)_nH$$

where m is 0, 1 or 2, R is hydrocarbyl containing from 1 to 24 carbons, including mixtures thereof, R', R" and R''' are independently hydrogen, methyl, or ethyl and when m is 2, each R''' can be different, and n averages 1 to 15.

Examples of such alcohol alkoxylates include glycol ethers such as ethylene glycol monomethyl ether (2-methoxyethanol) and propylene glycol monoethyl ether and the like and ethoxylates derived from mixed $C_2$ to $C_{24}$, preferably $C_2$ to $C_{18}$ and most preferably $C_6$ to $C_{12}$ straight chain alcohols. Suitable ethoxylates where R" and R" are hydrogen and m in the formula is 0, and n in the formula averages about 2 to 12, and preferably 3 to 6, are commercially available under the Ethonic trademark.

The promoters are used in minor, effective amounts, for example, from about 0.001 to 0.040 moles per mole of alpha-olefin monomer (0.1 to 4.0 mole percent). In general, the $BF_3$ is used in molar excess to the amount of promoter. This can be accomplished by using a closed reactor and a small $BF_3$ pressure over the reaction mixture. The promoter can be mixed with the olefin feed and the reaction can be carried out in a batch or continuous process at temperatures of about 0° to 200° C. and pressures ranging from atmospheric up to, for example, 1,000 psig. The reaction temperature will change the oligomer distribution with temperatures of about 50° C. and above favoring the production of lower oligomers, namely dimer. Preferred reaction temperatures and pressures are about 20° to 65° C. and 5 to 100 psig.

The oligomer mixture from the reaction contains monomer which can be removed by distillation. The monomer has been found to contain mostly less reactive, isomerized material. However, this monomer can be recycled because it will react to form oligomers in the presence of fresh alpha-olefin monomer. For example, portions of up to about 25 weight percent and preferably 5 to 15 weight percent recycled monomer based on total monomer can be mixed with fresh monomer. The product mixture can be further separated by distillation to provide one or more product fractions having the desired viscosities for use in various lubricant applications such as drilling, hydraulic or metal working fluids, gear oils and crankcase lubricants.

The alcohol alkoxylates in the presence of $BF_3$, form stable complexes which separate from the product mixture on standing and can be readily recovered and reused. This avoids the $BF_3$ separation and recovery procedures necessary when using, for example, a $BF_3$-butanol complex. In fact, because the alcohol ethoxylates are surfactants, it is preferable to let the catalyst settle from the reaction mixture prior to quenching with base, and especially when using NaOH, in order to avoid the formation of an emulsion.

The oligomer product can be hydrogenated by conventional methods. Supported nickel catalysts are useful. For example, nickel on a Kieselguhr support gives good results. Batch or continuous processes can be used. For example, the catalyst can be added to the liquid and stirred under hydrogen pressure or the liquid may be trickled through a fixed bed of the supported catalyst under hydrogen pressure. Hydrogen pressures of about 100 to 1,000 psig at temperatures of about 150° to 300° C. are especially useful.

The preparation of the fluids for use in the invention is further illustrated by, but is not intended to be limited to, the following examples in which the oligomerizations are performed in a three pint stirred reactor consisting of a glass reactor bowl, glass jacket, and a stainless steel top. The reactor is equipped with an air driven magnetic drive stirrer with a marine propeller, a heating/cooling coil and circulating system, dip tube, gas inlet and outlet valves and a pressure relief valve.

EXAMPLES 1-5

1-Decene (600.0 grams, 4.29 moles) and 1.0 mole % based on 1-Decene of Ethonic ® 610-3, (which is a $C_6$ to $C_{10}$ mixed alcohol ethoxylate having an average of three $—CH_{2l}—_{CH_2}O—$ groups), are charged into the reactor which is then assembled and purged with $N_2$ with gentle agitation for 30 minutes. During this time the reactor is brought up to the appropriate reaction temperature by the heating coil circulating system. The reactor is then pressurized ($N_2$) to 20 psig to insure that no leaks exist. After the pressure is relieved the stirring rate is increased and $BF_3$ is introduced into the reactor via a sparge tube located below the surface of the liquid. After a brief (5-10 seconds) purge, the system is pressurized to 10 psig with $BF_3$. The reaction is stopped after the chosen reaction time by venting the $BF_3$ through a 10 weight percent NaOH scrubber and quenching with either 5% aqueous NaOH (Examples 2 and 3) or saturated $Na_2SO_4$ (Examples 1, 4 and 5) (50-150 ml). The reactor is purged with dry $N_2$ until all of the $BF_3$ is removed. The polyalphaolefin (PAO) - unreacted decene mixture is washed several times with water, dried over anhydrous $CaCl_2$, and filtered. The product content is determined by gas chromatographic analysis. The reaction times, temperatures and product analysis are given in Table 1.

TABLE 1

| Example | Time (min) | Temp. (°C.) [Max.] | GC Area %[1] Monomer | Dimer | Trimer | Tetramer |
|---|---|---|---|---|---|---|
| 1 | 120 | 20 [28] | 11 | 41 | 42 | 6 |
| 2 | 120 | 32 [39] | 15 | 48 | 32 | 4 |
| 3 | 120 | 45 [50] | 23 | 48 | 20 | 9 |
| 4 | 60 | 45 [52] | 29 | 50 | 19 | 3 |
| 5 | 120 | 80 [86] | 14 | 68 | 16 | 3 |

Where area % ~ weight %

EXAMPLE 6

The process of Example 2 is repeated except at double the amount of alcohol ethoxylate (4 wt %/2 mole %) and quenching is with saturated $Na_2SO_4$. The product distribution in gas chromatography area percent is 9% monomer, 48% dimer, 37% trimer and 6% tetramer.

EXAMPLE 7

The process of Example 3 is repeated except that quenching is with saturated $Na_2SO_4$ and 9.1 weight percent of the decene monomer is recycled, considerably isomerized monomer from a previous reaction. The product distribution in gas chromatography area percent is 20% monomer, 52% dimer, 24% trimer and tetramer.

EXAMPLE 8

The process of Example 2 is repeated except that Ethonic ® 810-6 (2.8 wt %, 1.0 mole %) which is a $C_8$ to $C_{10}$ mixed alcohol ethoxylate having an average of six —$CH_2$—$CH_2O$—groups is used as the promoter and quenching is with saturated $Na_2SO_4$. The product distribution in gas chromatography area percent is 24% monomer, 46% dimer, 26% trimer and 4% tetramer.

The dimer fractions from Examples 1, 2 and 3 are separated by distillation and hydrogenated. Their physical properties are reported in Table 2 where the composition is given in gas chromatography area percent.

TABLE 2

| Example | 1 | 2 | 3 |
| --- | --- | --- | --- |
| Monomer | — | 0.5 | 0.7 |
| Dimer | 98.9 | 96.7 | 97.9 |
| Trimer | 1.1 | 2.6 | 1.4 |
| Tetramer | — | 0.2 | — |
| $KV_{100° C.}$(cSt) | 1.71 | 1.66 | 1.63 |
| $KV_{40° C.}$(cSt) | 5.22 | 4.99 | — |
| $KV_{-40° C.}$(cSt) | 266.0 | 251.0 | 257.0 |
| Pour Point (°C.) | <−65 | <−65 | <−65 |
| Flash Point (°C.) | 160.0 | 148.0 | 152.0 |

EXAMPLE 0 A-E

This example illustrates the recycle of the promoter/-$BF_3$ co-catalyst complex.

1-Decene (600.0 g, 4.29 mol) and Ethonic ® 610-3 ethoxylate (11.79 g, 42.9 mmol) are charged into the reactor which is then assembled and purged with N: with gentle agitation for 30 minutes; during this time the vessel temperature is brought up to 45° C. The reactor is then pressurized ($N_2$) to 20 psig to insure that no leaks exist. After the pressure is relieved, the stirring rate is increased and $BF_3$ is introduced into the reactor via a sparge tube located below the surface of the liquid. After a brief (5–10 seconds) purge, the system is pressurized to 10 psig with $BF_3$. Periodic samples are collected and quenched with saturated aqueous $Na_2SO_4$, washed with water (twice), dried over anhydrous $CaCl_2$, filtered through syringe disk filters, and analyzed by gas chromatography.

After 60 minutes, the $BF_3$ is purged from the reactor with $N_2$ for about 30 minutes. The stirring is then stopped to allow the two existing phases to separate (~20 minutes). The upper layer (product 9A) is then drained and washed with 5% aqueous NaOH followed by 2 water washes. The lower layer (co-catalyst) remains in the reactor.

At this point more 1-decene is added and a second reaction initiated by pressurizing the reactor with $BF_3$ (no 25 additional Ethonic ®610-3 is added). After 60 minutes the mixture is again purged with $N_2$, allowed to settle (20 minutes), and the PAO drained (9B). This procedure is repeated once more to collect a third lot of PAO (9C).

After the third run, the co-catalyst layer is kept in the reactor under an atmosphere of $BF_3/N_2$. After 20 hours another run (120 minutes) is made to collect a fourth lot of PAO (9D). Again, after an additional 20 hours, a fifth run is made (9E). Results are tabulated in Table 3.

TABLE 3

| Reaction | Time (min) | GC Area % Monomer | Dimer | Trimer | Tetramer |
| --- | --- | --- | --- | --- | --- |
| 9A | 60 | 26 | 50 | 21 | 3 |
| 9B | 60 | 44 | 42 | 12 | 1 |
| 9C | 60 | 46 | 41 | 12 | 1 |
| 9D | 120 | 29 | 54 | 16 | 2 |
| 9E | 120 | 34 | 50 | 14 | 1 |

The results illustrate that the co-catalyst can be easily recycled an remains effective in providing high yields of dimer.

EXAMPLE 10

Example 3 is repeated using 2-methoxyethanol promoter at a concentration of 1 mole percent based on monomer. After two hours the gas chromatography area percent product distribution is 8% monomer, 77% dimer, 13% trimer and 2% tetramer or about 85% dimer based on total oligomer product with a conversion to oligomer of over 90%. Repeating the process at double the promoter concentration [2.0 mol % (1.0 wt %)] gave about the same result in half the time (one hour instead of two). This example illustrates that an oligomer which is close to a 2 cSt (at 100° C.) viscosity product can be produced by merely removing the monomer.

COMPARISON

A product prepared from 1-decene monomer using a $BF_3$.N-BUTANOL catalyst (1.3 mole percent n-butanol on monomer) at a reaction temperature of 40° C. and 20 psig $Bf_3$ pressure typically gives a gas chromatography area percent product distribution of about 1% monomer, 2% dimer, 53% trimer, 28% tetramer, 11% pentamer, and 5% hexamer.

Samples of eicosane (linear $C_{20}$) and 9-methylnonadecane were obtained. The 9-methylnonadecane was synthesized by the dimerization of 1-decene using tri-n-octyl aluminum followed by hydrogenation. This procedure is known to give 9-methylnonadecane as the predominant $C_{20}$ product. A sample of 2-methoxyethanol generated hydrogenated decene dimer prepared according to Example 10 was spiked with eicosane and 9methylnonadecane and analyzed by gas chromatography. No 9-methylnonadecane isomer was detected (less than 0.5 weight percent) in the unspiked sample. The retention time of the 9-methylnonadecane was the same as the relatively linear isomer in the 1-butanol/1-propanol generated material. Subsequently, GC/MS analysis confirmed that this isomer was 9-methylnonadecane. No eiscosane was observed in either product.

Samples of the 2-methoxyethanol generated dimer were then spiked with varying amounts of 9-methylnonadecane and the $KV_{-54° C.}$ values determined with the results shown below:

TABLE 4

| Entry | % Isomer Added | $KV_{-54° C.}$ (20 min) | $Kv_{-54° C.}$ Final | Comments |
| --- | --- | --- | --- | --- |
| A | 0% | 1030 cSt | 1030 cSt | Clear, no vis. change |
| B | 1% | 1070 cSt | 1060 cSt | Sl. cloudy, 1.5 hour |
| C | 3% | 2110 cSt | 1160 cSt | Cloudy - 15 minutes |
| D | 5% | 1790 cSt | 1200 cSt | Cloudy - 10 minutes |
| Compar- | 0% | 1470 cSt[1] | 1220 cSt[2] | Cloudy |

TABLE 4-continued

| Entry | % Isomer Added | KV$_{-54°C}$ (20 min) | Kv$_{-54°C}$ Final | Comments |
|---|---|---|---|---|
| ison | | | | |

[1] at 30 minutes
[2] at 1 hour

Entries C and D behave similarly to decene dimer PAO samples derived from 1-butanol/1-propanol co-catalyzed reactions (see "Comparison" in Table 4 which is a hydrogenated dimer derived from a BF$_3$/1-propanol catalyzed reaction), i.e. the KV$_{-54°C}$ values were initially high and gradually decreased with time while the mixture became cloudy. The cloud point of a commercially available 2.0 cSt PAO fluid, which consisted of very pure decene dimer, was −57° C. compared to a cloud point of < −70° C. for a 2-methoxyethanol generated dimer of the invention. These results demonstrate that the dimer products of the invention have significantly improved physical properties caused by a difference in composition from prior 1-decene dimer compositions.

EXAMPLE 11

1-Octene (750.0 grams, 6.70 moles) and 2-methoxyethanol (5.09 grams, 67.0 mmoles) were charged into the reactor which was then assembled and purged with N: with gentle agitation for 30 minutes. During this time the vessel was heated to 45° C. with the circulating system. The stirring rate was increased (rpm not measured) and BF$_3$ was introduced into the reactor via a sparge tube located below the surface of the liquid. After a brief (5-10 seconds) purge, the system was pressurized to 10 psig with BF$_3$. An exotherm occurred which reached a maximum temperature of 64° C. at ~15 minutes.

The reaction was stopped by venting the BF$_3$ through a 10% NaOH scrubber and then quenching with 5% aqueous NaOH (100 mL). The reaction mixture was separated from the quenching medium, washed several times with water, allowed to settle, and filtered through filter paper.

The product contained 5% C$_8$, 64% C$_{16}$, 25% C$_{24}$, and 6% C$_{32}$ (normalized gas chromatography area percent).

The crude oligomerization product (1200 g) was hydrogenated in a 2-liter autoclave using a Ni/Kieselguhr catalyst (48 g) at 200° C. and 500 psig H$_2$ for 2 hours. After cooling, the product was filtered through filter-aid to give the crude hydrogenated product. The distillation was carried out at 1.5 mm Hg and the fraction boiling at 107°-120° C. was collected to give 535 g (1071 g feed) of pure hydrogenated octene dimer. The physical properties were as follows:

| | |
|---|---|
| KV$_{100°C}$ | 1.09 cSt |
| KV$_{40°C}$ | 2.69 cSt |
| KV$_{-40°C}$ | 71.0 cSt |
| Pour point | < −65° C. |
| Flash point | 122° C. |

The target specifications for an IEC 296 - Class III and IIIA transformer fluid are:

| | |
|---|---|
| KV$_{40°C}$ | 3.5 cSt max |
| KV$_{-40°C}$ | 150 cSt max |
| Pour point | −60° C. max |
| Flash point | 95° C. min |

In such use the fluid is contained in an electrical apparatus, i.e. a power transformer. The fluid surrounds an electrical component in the apparatus and acts as an electrical insulating and heat removal medium.

The physical properties of the octene dimer exceeded the transformer fluid specifications and demonstrated excellent low temperature performance.

The dimer oils of the invention can be used neat in various heat transfer, insulating and lubricant applications, and when used in insulating, functional fluid and/or lubricating oil applications such as, for example, electro erosion, high speed aluminum cold rolling, transformer and switchgear oil, shock absorber, brake, hydraulic textile covering and spindle fluids, drilling muds and the like, their properties can be enhanced by the use of conventional oil additives in total amounts of up to about 25 weight percent and preferably from about 0.1 to 20 weight percent. Such additives include, for example, dispersants, anti-oxidants, anti-wear agents, anti-foam, corrosion inhibitors, detergents, seal swell agents, etc. These types of additives are well known in the art. Some examples of such additives are zinc dialkyl-dithiophosphates, calcium aryl sulfonates, overbased calcium aryl sulfonates, barium phenates, barium oxide neutralized reaction products of phosphorus pentasulfide and terpenes or high molecular weight olefins, hindered alkyl phenols, methylene-bis-dialkyl phenols, dibutyl tin sulfide, dibutyl hydrogen phosphonate, tri-cresyl-phosphate, high molecular weight alkyl succinimides of ethylene-polyamines such as tetraethylene-polyamine, sulfur-bridged alkyl phenols, sulfurized fatty acid esters and amides, silicones, dialkylesters, and the like. Mixtures of the C$_8$ to C$_{10}$ dimer oils in any proportions can be used. The dimer compositions can contain minor amounts of higher oligomers (trimer, tetramer, etc.) but preferably contain at least 60 weight percent and more preferably at least 75 weight percent of dimers. The dimer oils can be used as additive oils or as base oils and in blends with mineral oils and with other synthetic oils such as, for example, synthetic esters.

What is claimed is:

1. A heat transfer, lubricating, and/or insulating fluid composition which comprises (i) a synthetic oil selected from the group consisting of 1-octene dimer, 1-decene dimer, codimer of 1-octene dimer further consists of a mixture of C$_{16}$H$_{32}$ isomers, which mixture includes 7-methylpentadecene isomers, provided that said mixture contains less than about 2.5 weight percent of said 7-methylpentadecene isomers based on the weight of said mixture, (b) said 1-decene dimer further consists of a mixture of C$_{20}$H$_{40}$ isomers, which mixture includes 9-methylnonadecene isomers, provided that said mixture contains less than about 2.5 weight percent of said 9-methylnonadecene isomers based on the weight of said mixture, and (c) said co-dimer further consists of a mixture of C$_{18}$H$_{36}$ isomers, which mixture includes C$_{18}$H$_{36}$ isomers selected from the group consisting of 7-methylpentadecene, 9-methylheptadecene isomers, and mixtures thereof, provided that said mixture contains less than about 2.5 weight percent of said 7-methylpentadecene and 9-methylheptadecene isomers based on the weight of said mixture, and (ii) from about 0.1 to 2.5 weight percent of fluid composition of one or more oil additives.

2. The fluid composition of claim 1 wherein said oil additives are selected from dispersants, antioxidants, anti-wear agents, anti-foam agents, corrosion inhibitors, detergents and seal swell agents.

3. The fluid composition of claim 1 wherein said synthetic oil is hydrogenated so as to provide $C_{16}H_{34}$ isomers containing less than about 2.5 weight percent of 7-methylpentadecane, $C_{20}H_{42}$ isomers containing less than about 2.5 weight percent of 9-methylnonadecane and $C_{18}H_{38}$ isomers containing less than about 2.5 weight percent of 7-methylheptadecane and/or 9-methylheptadecane.

4. The fluid composition of claim 3 wherein said $C_{16}H_{34}$ isomers contain less than about 0.5 weight percent 7-methylpentadecane, said $C_{20}H_{42}$ isomers contain less than about 0.5 weight percent 9-methylnonadecane and said $C_{18}H_{38}$ isomers contain less than 0.5 weight percent 7-methylheptadecane and/or 9-methylheptadecane.

5. The fluid composition of claim 3 wherein said synthetic soil consists of $C_{16}H_{34}$ isomers.

6. The fluid composition of claim 2 wherein said synthetic oil consists of $C_{20}H_{42}$ isomers.

7. The fluid composition of claim 2 wherein said synthetic oil consists of $C_{18}H_{38}$ isomers.

8. The fluid composition of claim 2 wherein said synthetic oil consists of $C_{16}H_{34}$, $C_{18}H_{38}$ and $C_{20}H_{42}$ isomers.

* * * * *

UNITED STATES PATENT AND TRADEMARK OFFICE
CERTIFICATE OF CORRECTION

PATENT NO. : 5,171,918
DATED : December 15, 1992
INVENTOR(S) : Ronald L. Shubkin, et al It is certified that error appears in the above-indentified patent and that said Letters Patent is hereby corrected as shown below:

Column 8, claim 1 line 4, should read --of 1-octene and 1-decene, and mixtures thereof wherein (a) said 1-octene dimer--

Column 9, claim 1, line 22, should read --0.1 to 25.. --

Column 10, claim 5, line 2, should read --..oil consists of..--
Column 10, claim 6, line 1, change "claim 2" to read --claim 3--
Column 10, claim 7, line 1, should read --..of claim 3..--
Column 10, claim 8, line 1, should read --of claim 3. ..--

Signed and Sealed this

Twenty-fifth Day of January, 1994

Attest:

BRUCE LEHMAN

Attesting Officer   Commissioner of Patents and Trademarks